(12) United States Patent
Streit (10) Patent No.: US 11,666,694 B2
(45) Date of Patent: Jun. 6, 2023

(54) DEVICE FOR SEPARATION OF FLUID BIOLOGICAL MATERIAL, A SEPARATING FLOAT AND A KIT

(71) Applicant: BELLEMED INNOVATIONS S.R.O., Ostrava (CZ)

(72) Inventor: Libor Streit, Ujezd u Brna (CZ)

(73) Assignee: BELLEMED INNOVATIONS S.R.O., Ostrava (CZ)

(*) Notice: Subject to any disclaimer, the term of this patent is extended or adjusted under 35 U.S.C. 154(b) by 275 days.

(21) Appl. No.: 16/753,034

(22) PCT Filed: Oct. 3, 2017

(86) PCT No.: PCT/CZ2017/050046
§ 371 (c)(1),
(2) Date: Apr. 2, 2020

(87) PCT Pub. No.: WO2019/068271
PCT Pub. Date: Apr. 11, 2019

(65) Prior Publication Data
US 2020/0289720 A1    Sep. 17, 2020

(51) Int. Cl.
*A61M 1/00*  (2006.01)
*B01L 3/00*  (2006.01)

(52) U.S. Cl.
CPC .......... *A61M 1/63* (2021.05); *B01L 3/50215* (2013.01); *A61M 2202/08* (2013.01);
(Continued)

(58) Field of Classification Search
CPC .... A61M 1/63; B01L 3/50215; B01L 3/5021; B01L 2300/041; B01L 2300/06; B01L 2300/0832; B01L 2300/0861
See application file for complete search history.

(56) References Cited

U.S. PATENT DOCUMENTS

| 2009/0221075 | A1* | 9/2009 | Dorian | C12M 47/02 |
| | | | | 435/308.1 |
| 2011/0251041 | A1* | 10/2011 | Chavarria | B01D 17/0217 |
| | | | | 494/37 |
| 2014/0363891 | A1* | 12/2014 | Llull | C12M 45/09 |
| | | | | 435/378 |

FOREIGN PATENT DOCUMENTS

| WO | 2009111338 A1 | 9/2009 | |
| WO | WO-2009111338 A1 * | 9/2009 | ............ B01L 3/5021 |

(Continued)

OTHER PUBLICATIONS

International Search Report and Written Opinion in Corresponding PCT Application No. PCT/CZ2017/050046 dated Jun. 22, 2018. 12 pages.

*Primary Examiner* — Christopher Adam Hixson
(74) *Attorney, Agent, or Firm* — Leason Ellis LLP (57) ABSTRACT

The invention relates to a device for separation of fluidal biological material components, particularly separation of components of the material collected by liposuction for subsequent transfer of the adipose tissue in an injection form. The device comprises a container with an outlet duct arranged in it, the outlet duct having its upper end adapted for collecting the material, and its lower end that is in fluid communication with the inner space of the container at its bottom. Further, the invention relates to a separating float for separation of the fluidal biological material components, the float being intended to be used in the device, wherein the float comprises at least one by-pass opening for passage of the fluidal biological material contained in the container from the area below the separating float into the area above it. The invention also relates to a kit including the device and the float.

9 Claims, 8 Drawing Sheets

(52) U.S. Cl.
CPC ..... *B01L 2300/041* (2013.01); *B01L 2300/06* (2013.01); *B01L 2300/0832* (2013.01); *B01L 2300/0861* (2013.01)

(56) References Cited

FOREIGN PATENT DOCUMENTS

| WO | 2010065018 A1 | 6/2010 | |
| WO | WO-2010065018 A1 * | 6/2010 | ............. B01L 3/502 |
| WO | 2011103173 A2 | 8/2011 | |
| WO | 2012116100 A1 | 8/2012 | |
| WO | WO-2012116100 A1 * | 8/2012 | .......... A61M 1/0005 |
| WO | 2013106655 A1 | 7/2013 | |
| WO | 2014039697 A1 | 3/2014 | |
| WO | WO-2014039697 A1 * | 3/2014 | ............. A61K 35/35 |
| WO | 2017078563 A1 | 5/2017 | |
| WO | WO-2017078563 A1 * | 5/2017 | ............. A61K 35/12 |

\* cited by examiner

DEVICE FOR SEPARATION OF FLUID BIOLOGICAL MATERIAL, A SEPARATING FLOAT AND A KIT

CROSS-REFERENCE TO RELATED PATENT APPLICATIONS

This application is a U.S. National Stage Application under 35 U.S.C. § 371 of International Patent Application No. PCT/CZ2017/050046, filed Oct. 3, 2017, which is incorporated by reference in its entirety. The International Application was published on Apr. 11, 2019, as International Publication No. WO 2019/068271 A1.

FIELD OF THE INVENTION

The present invention relates to a device for separation of the components of fluid biological material, particularly for separation of components of the material collected by liposuction for the subsequent transfer of the adipose tissue in the form of injection. Further, the invention relates to a float for the separation of the fluid biological material components, which is used in the device according to the present invention. The invention also relates to a kit containing the device and the float.

STATE OF THE ART

Transfer of the adipose tissue in the injection form is called lipofilling, fat grafting, lipotransfer, lipografting, in the specialized terminology, or using Czech terms it is called lipoinjection, transfer of adipose tissue or sometimes even simply surgery with one's own fat (for instance, enlargement of breasts with one's own fat). In plastic and reconstruction surgery of breast the Czech term "lipomodelling of breast" is the most appropriate.

Regardless of the term used, the basic principles of the surgery remain the same.

The transfer of the adipose tissue consists of three consecutive steps: 1) adipose tissue collection, 2) processing and 3) application.

The processing technique has an essential influence on the quality of the adipose graft. In the clinical practice, the adipose tissue is most frequently processed using three basic physical principles, comprising sedimentation, centrifugation and filtration through a filtration membrane.

The collected adipose tissue (lipoaspirate) is a mixture of the adipose tissue fragments, fat droplets, cellular detritus, tumescent solution and blood. It is the object of further processing of the lipoaspirate to obtain a purified cellular mixture.

Figure 1:
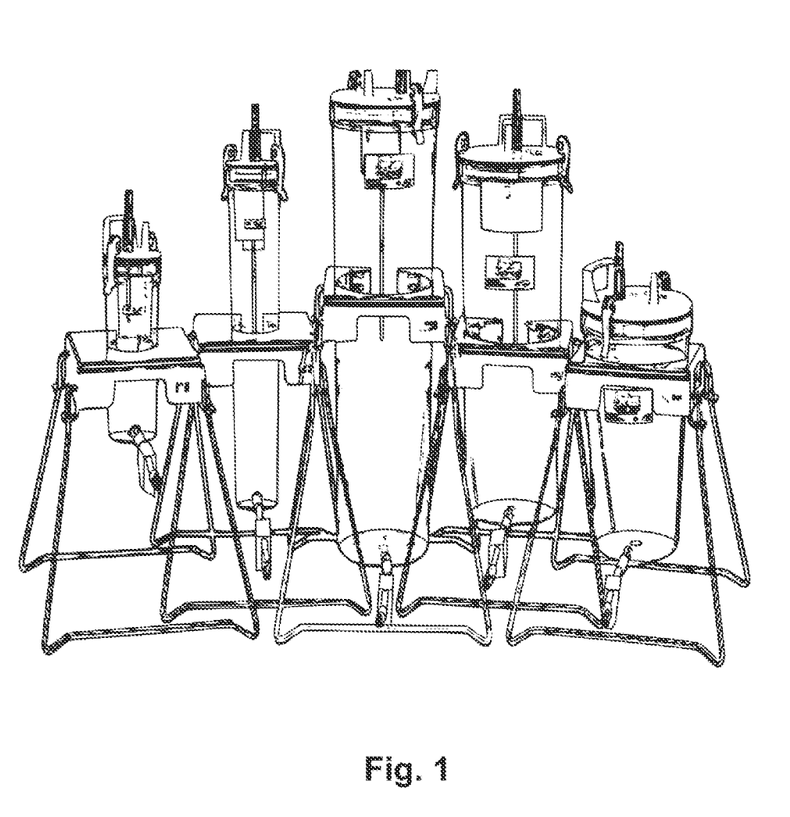
FIG. 1 shows canisters for the adipose processing by sedimentation.

The sedimentation is the simplest technique used—FIG. 1, wherein the individual components of the lipoaspirate are separated from each other by effect of the gravitation force. It is possible to collect the adipose tissue manually into syringes, in which the lipoaspirate is allowed to sediment; the lower watery layer is then simply let out of the syringe. The sedimentation principle is used even in more recent commercially available lipoaspirate collectors that can be directly interconnected with a collecting cannula and with a vacuum pump by means of a hose. These collectors can be arranged directly on the operating table, some of them are sterilizable, the base of the collector can usually be provided with an outlet for the watery component of the lipoaspirate. A high content of the watery components (tumescent solution etc.) and residues of the damaged cells in the processed adipose tissue, as well as the downtime during the surgery are the disadvantages of sedimentation.

Nowadays, centrifugation is the most frequently used technology of the lipoaspirate processing. It was popularized by Coleman, who described in details the processing technology of the adipose tissue by three-minute centrifugation using the relative centrifugal force of 1286 g. The centrifugation is performed directly in the collecting syringes (most often in 10 ml, according to Coleman). The lipoaspirate is divided into 4 layers by the centrifugation. The upper "oil layer" contains glyceride from vacuoles of the disintegrated adipose cells. Below the upper layer, there is the "adipose tissue layer", which is most frequently separated as a whole from the other layers and then it is used for the transfer itself. Below said layer, there is the light pink "watery layer", which contains a tumescent solution and plasma components. The last lower layer (sediment), in literature usually referred to as a pellet, contains residues of the connective tissue, erythrocytes, leucocytes and other nucleate cells. After the centrifugation, the plug from the syringe stopper is loosened and the lower watery layer is allowed to go out freely, whereas also the fraction "pellet" is removed from the base. The upper adipose layer can be removed by pouring out, by means of turning the syringe over, or it can be removed by suction.

A great number of handlings and work in open space are the disadvantages of the centrifugation technique. The impossibility of the collection in another way than manually, which is physically demanding and lengthy, is another disadvantage.

Figure 2:
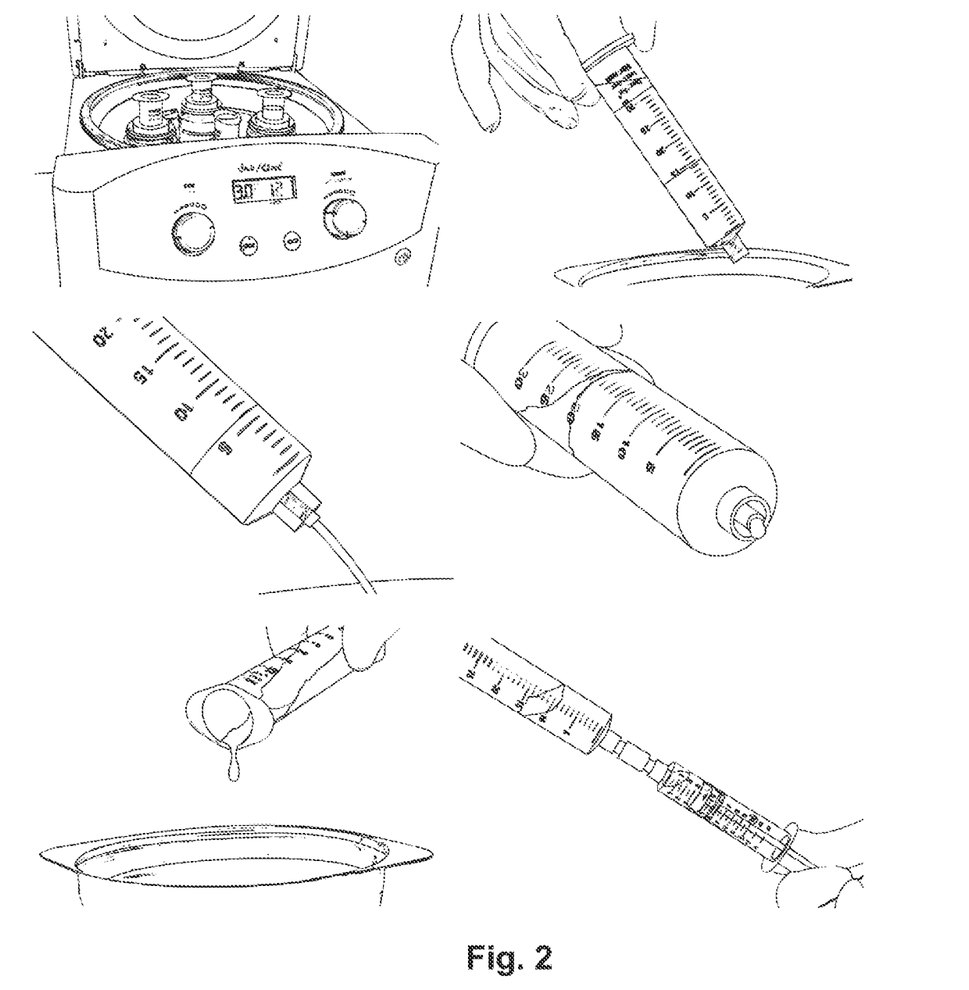
FIG. 2 shows centrifugation of lipoaspirate.
Figure 3:
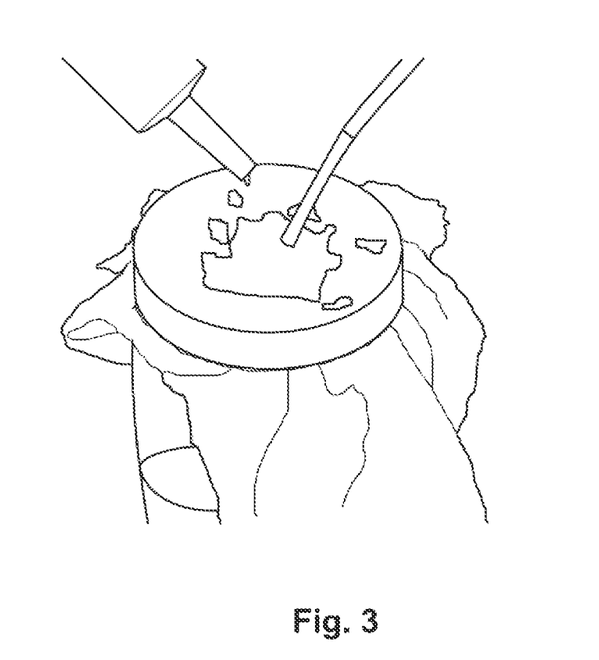
FIG. 3 shows filtration and washing through a membrane.
Figure 4:
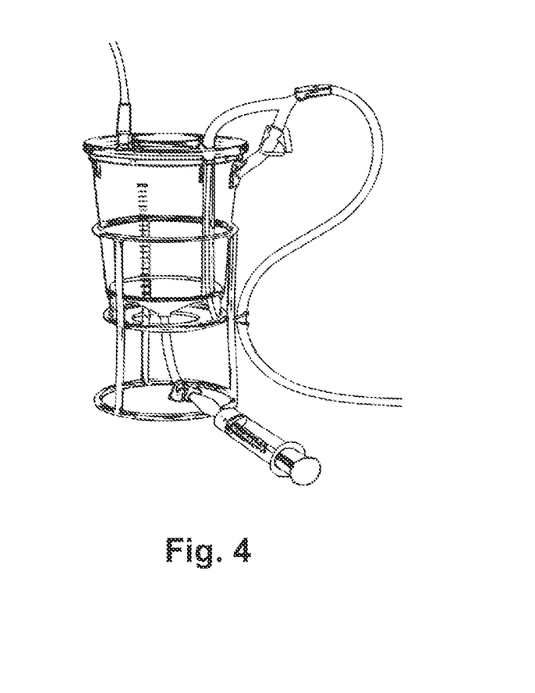
FIG. 4 shows a canister for the adipose processing by filtration.

The centrifugation of the collected adipose tissue in 30 ml collecting syringes and the subsequent removal of the lower watery layer by means of simple loosening the syringe stopper can be seen on the photos in FIG. 2. By turning the syringe over, the upper oil layer can be removed; pouring the adipose tissue out can be prevented by applying a mull that at the same time absorbs the oil layer residua (not illustrated in FIG. 2). The last photo captures the transfer of the processed adipose tissue into the 10 ml application syringes. The filtration through the filtration membrane (FIG. 3) is the third basic used principle of the lipoaspirate processing. There can be various means of realization thereof. The filtration and washing with a physiological solution through the filtration membrane placed on the top of the container may be the simplest; afterwards, the purified adipose is transferred into the application syringes manually. The drawbacks are obvious; the tissue is processed in open space, the number of handlings of the graft is relatively great.

More sophisticated systems working on the filtration principle are commercially available. They use filtration units in the form of canisters that can be disposable or sterilizable. The hose draining the lipoaspirate from the liposuction cannula is connected to the inlet part of the unit, most often to the opening in the container cover. Vacuum in the inlet part of the unit is provided by connecting a vacuum pump to another opening in the inlet part of the container, using a connecting hose. The inlet part of the unit is separated from the discharge part by means of a membrane, through which the filtration proceeds. The waste fluid biological material is removed from the outlet part of the container through a discharge hole, or in another way.

Figure 5:
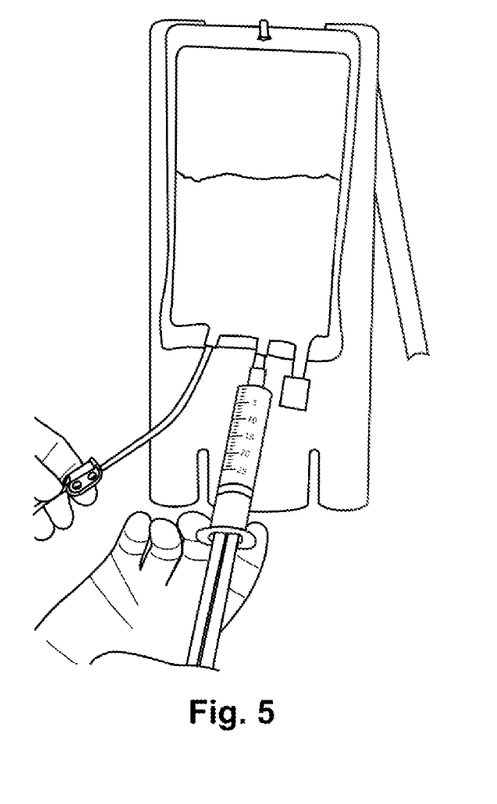
FIG. 5 shows washing and filtration of the lipoaspirate through a membrane in PureGraft™ system.

PureGraft™ sets by Puregraft LLC are further commercially available systems for the adipose processing using filtration. They are adapted for collection by manual liposuction using syringes. They have a form of bags that are divided inside into the inlet part and the outlet part by means of a double membrane. The washing and filtration of the lipoaspirate through the membrane in the system Pure-Graft™, particularly by filling up the bag, containing the lipoaspirate, with the Ringer solution while the outlet part is closed, is shown in FIG. 5.

All of the above mentioned techniques involve many drawbacks, including high time demands, contamination risk due to the sample handling in an open space, as well as the impossibility automation of the individual sub-steps.

SUMMARY OF THE INVENTION

The above mentioned disadvantages are solved by the device according to the invention, which comprises a container that has a bottom, a side wall and an outlet duct for suction (collection) of the processed adipose tissue from the base of the container upwards, namely (preferably) above the level at which the container is filled to the limit. The outlet duct is arranged in the container and has an upper end that is adapted for collecting material from the outlet duct, and a lower end that is in fluid communication with the container interior at its bottom. The container is not closed in its upper part and is adapted for an attachment of a lid, e.g. by means of a bayonet type of attachment, but also other types of the lid fastening are possible, e.g. with a thread, by means of clips, etc. Preferably, the container is translucent, more preferably transparent. In a preferred embodiment the bottom of the container at least partly slopes down towards the area of the fluid communication of the outlet duct with the container interior near its bottom. The outlet duct can be formed e.g. by a tube, which is arranged inside the container and the inner cavity of which creates the outlet duct, whereas the tube is arranged preferably coaxially aligned with the container.

The outlet duct, when the tube variant is considered, can be designed as an integral part of the container, as a separate part, or as a part of the lid. An integral part of the container means that the tube and the container form one piece. Fluid communication of the outlet duct with the area near the bottom of the container can be realized e.g. by means of holes and/or grooves at the end of the tube facing the container bottom. Preferably, the container is further provided with an externally widened edge of its upper end in order to facilitate its placement in a stand.

The device according to the invention preferably further comprises a lid, preferably provided with at least one handle for an easier handling of the device, e.g. when being drawn out of the centrifugal machine. The lid is provided with two openings, one opening being intended for an input of the biological material and adapted for connection to the collecting hose, to which the liposuction cannula is connected. The second opening is intended for connection of the suction hose that is connected to a vacuum pump/medical suction unit. Preferably, the hoses can be fitted hermetically to the openings by insertion into them (like a male connector) or by sliding onto them (like a female connector) or by means of a jumper. A lower part of the lid around the inlet opening, namely between the opening for the biological material input and the outlet duct, is provided with a vertical barrier that helps to prevent the entering biological material from contaminating the functional parts, specifically the mouth of the outlet duct or the output opening.

In a preferred embodiment, the container as well as the lid are adapted for a bayonet or airtight fitting of the lid to the container.

The invention further relates to a separating float that is insertable into the container in the direction parallel to the axis of the container interior, e.g. in order to separate the upper oil layer from the biological material sample, the float comprising at least one by-pass opening for the material contained in the container to pass from the space below the separating float to the space above it. Preferably, the separating float comprises at least one recess and/or at least partially slopes down in order to facilitate the material collection from the space above the separating float. Preferably, the separating float further comprises at least one auxiliary drainage channel for suction or collection of the material located above the separating float, wherein the lower end of the auxiliary drainage channel is in fluid communication with the space above the upper surface of the separating float, preferably in the position of the recess or in the area to which the partial slope of the float heads.

It will be evident to a person skilled in the art that the use of the separating float is not limited to the device according to the invention only but it can also be used in a different device or in a type of container different from that defined in attached patent claims.

In a preferred embodiment, the tube has a widened outer diameter to define the maximum possible insertion of the float into the container.

Preferably, both the outlet duct and the auxiliary drainage channel, or auxiliary drainage channels, are adapted for the connection of a hose with the male-type connector or the female-type connector for filling syringes, wherein the hose can also be attached by means of a jumper, or the outlet duct and/or the auxiliary channel can be ended directly by an ending adapted for the connection of a syringe. Preferably, the outlet duct height is larger than the height of the maximum level in case of filling the container to the maximum possible volume, and at the same time it is not too high in order to fit below the lid so that the airtightness could be secured.

The invention further relates to a kit for the separation of the fluidal biological material, particularly the adipose tissue, the kit comprising the container, the float and the lid, as defined above.

EXAMPLES

Example 1

Connection of the individual parts of the device and the principle of the separation The device according to the invention is adapted for an automated collection of the biological fluidal material, e.g.

lipoaspirate, and thus the collecting container 1 is a kind of a collecting canister. And it is also intended for a direct insertion into the centrifugal machine to be centrifuged. In this way, the lipoaspirate is divided into the individual layers described above. The separating float 8 is intended to separate and suck away the upper oil layer. The outlet duct 5 of the collecting container 1 is intended to suck away the waste watery layer and the pellet layer, i.e. the sediment, and subsequently to suck away (take up) the adipose tissue. It is intended to be connected to the hose with a connector for filling syringes.

The procedure of the adipose tissue processing includes the following steps:

Step 1

The collecting container 1 with the fitted and hermetically sealed lid 7 is placed into a stand, after which a collecting hose is connected by means of a male-type connecting connector to the inlet opening 14 arranged in the lid 7. The hose connection can be made even by a simple putting on the cap (adapted for it as a conical or step-like form of the male-type connector). The collecting hose is connected on its opposite end to the collecting liposuction cannula. A connecting hose intended to be connected to the suction unit/vacuum pump or another device to provide vacuum is connected to the outlet opening 15 arranged in the lid 7. The hose connection to the outlet opening 15 can be implemented in the variants described in connection with the inlet opening 14. The biological material is transported from the collecting liposuction cannula through the collecting hose into the container 1 by means of the vacuum brought about by the connection of the vacuum pump to the connecting hose.

Step 2

The collecting container 1, containing the biological material intended for the separation of its individual components, and closed with the lid 7, is inserted into the centrifuge and subjected to the centrifugation.

Step 3

The collecting container 1 is removed from the centrifuge, inserted into the stand for the collecting container 1 and the lid 7 is taken off.

Step 4

The separating float 8 is inserted into the collecting container 1 so that the oil layer may flow from the space below the float 8 to the space above the float 8 through the by-pass opening 10 or through the openings in the float 8. After that, the connecting hose for the connection with the suction device, e.g. the vacuum pump, is put on the auxiliary drainage channel 12 of the float 8, after which the oil layer is sucked out from the container 1, i.e. from the space above the float 8.

Step 5

The hose with the connector for filling syringes is put on the outlet of the outlet duct 5 of the collecting container 1 and the so-called waste layers, i.e. the watery layer and the pellet layer, are sucked off.

Step 6

In the end, the adipose tissue layer is collected through the outlet duct 5 of the collecting container 1 into e.g. syringes that are intended for the subsequent application.

Step 7

Then the float 8 is removed from the container 1, the lid 7 is put on and the complete process can be repeated.

Example 2

Figure 6:
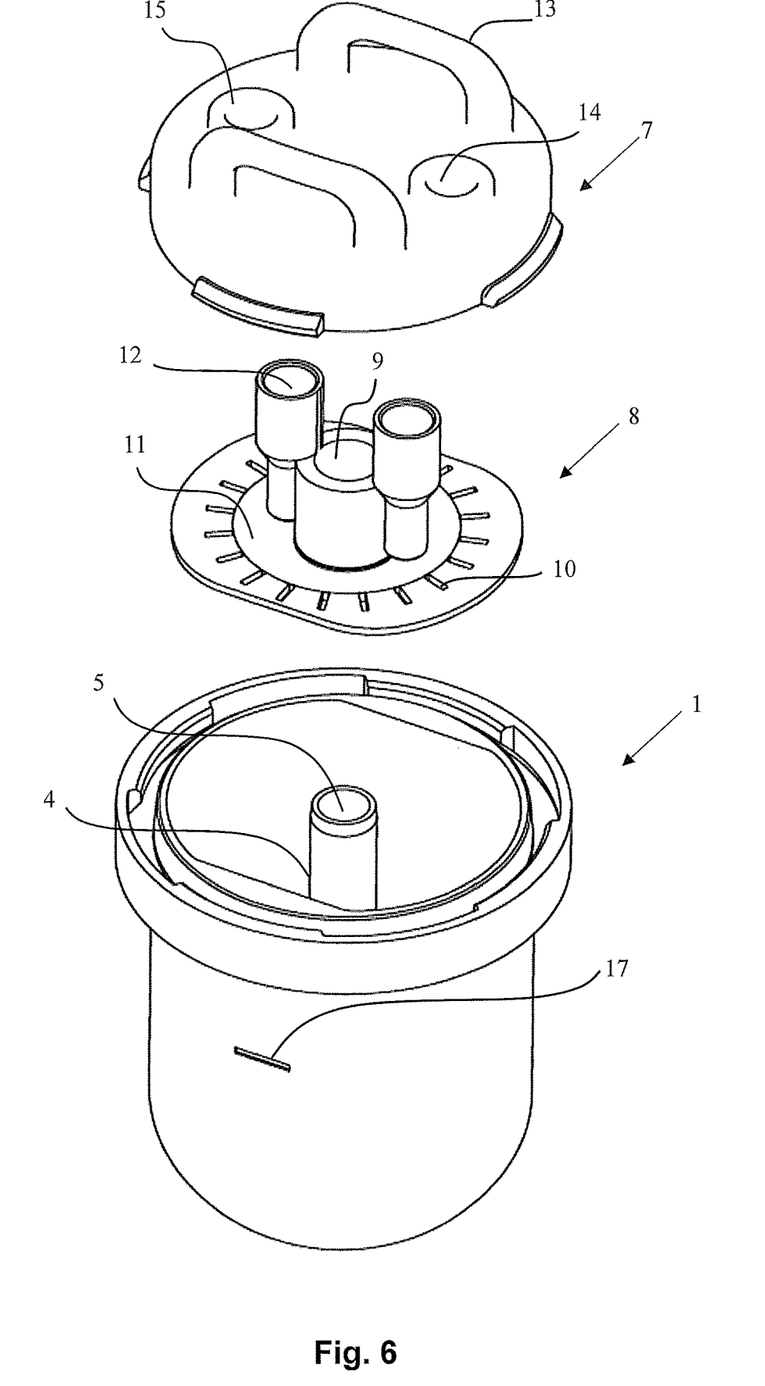
FIG. 6 is an exploded view on the kit according to the invention.

The kit or the medical device according to the invention, serving for processing of the adipose tissue, collected using liposuction, for the adipose tissue transfer in an injection form, shown in an exploded view in FIG. 6, is intended for the centrifugation, and consists of three main parts: a collecting container 1, a lid 7 of the collecting container 1, a separating float 8 that is intended to separate the upper oil layer after the lipoaspirate centrifugation. In a preferred embodiment, the kit further includes a hose (not shown) with a connector for filling syringes. A stand for the collecting container, connecting pieces for the hoses and a connecting hose represent supplementary parts.

The kit, shown in FIG. 6, comprises the container 1 that has a bottom 2, a side wall 3 and an upper inlet opening intended for putting the lid 7 on. A part of the bottom 2 of the container 1 slopes down towards the container 1 axis. The side wall 3 above the bottom 2 of the container 1 can have a cylindrical inner surface or can also have a different cross-section as far as it is adapted so that the separating float 8 can be inserted into the container 1 along a predetermined path.

Figure 8:
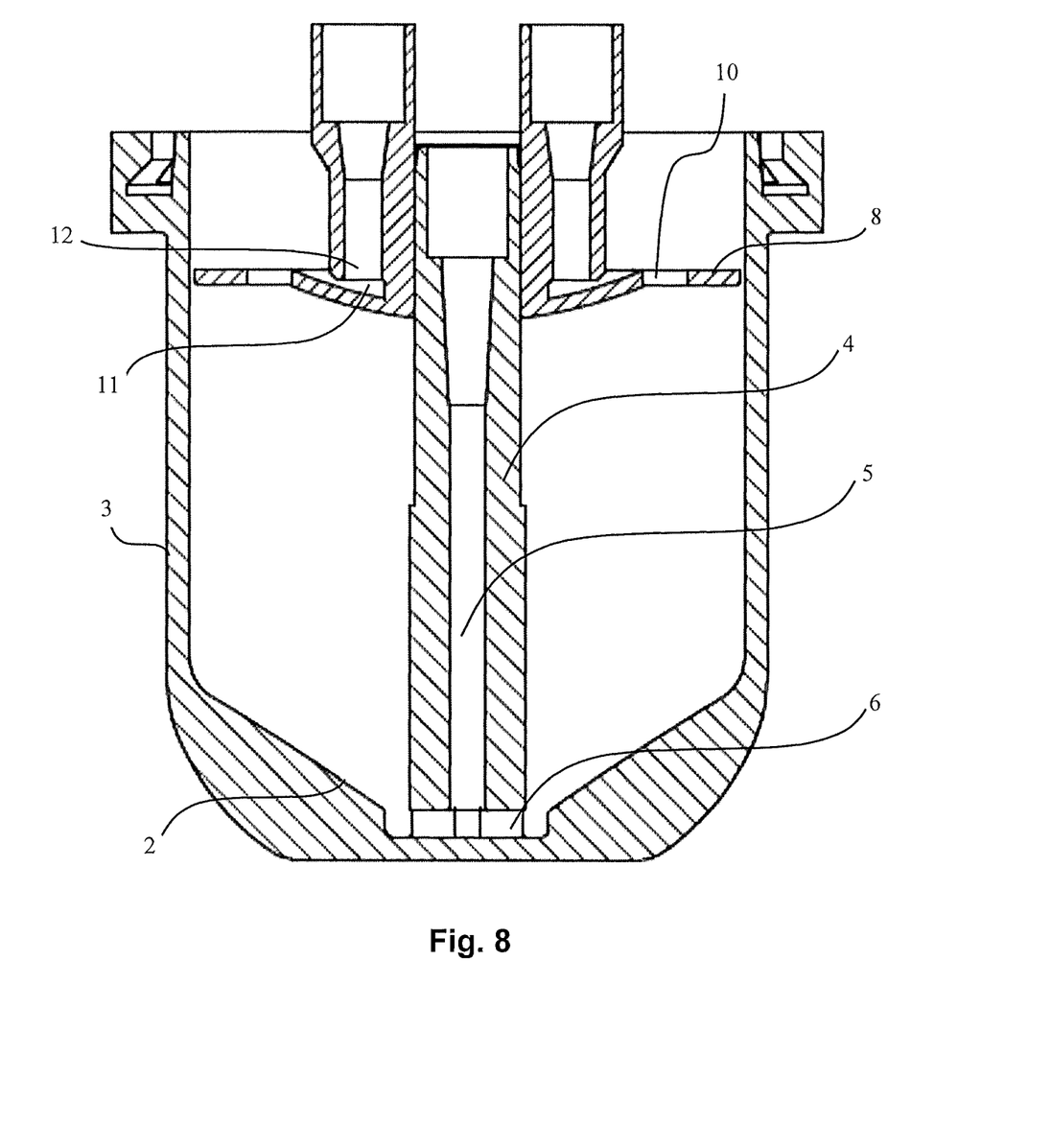
FIG. 8 is a cross-section view of the container according to the invention into which the float is inserted.
Figure 9:
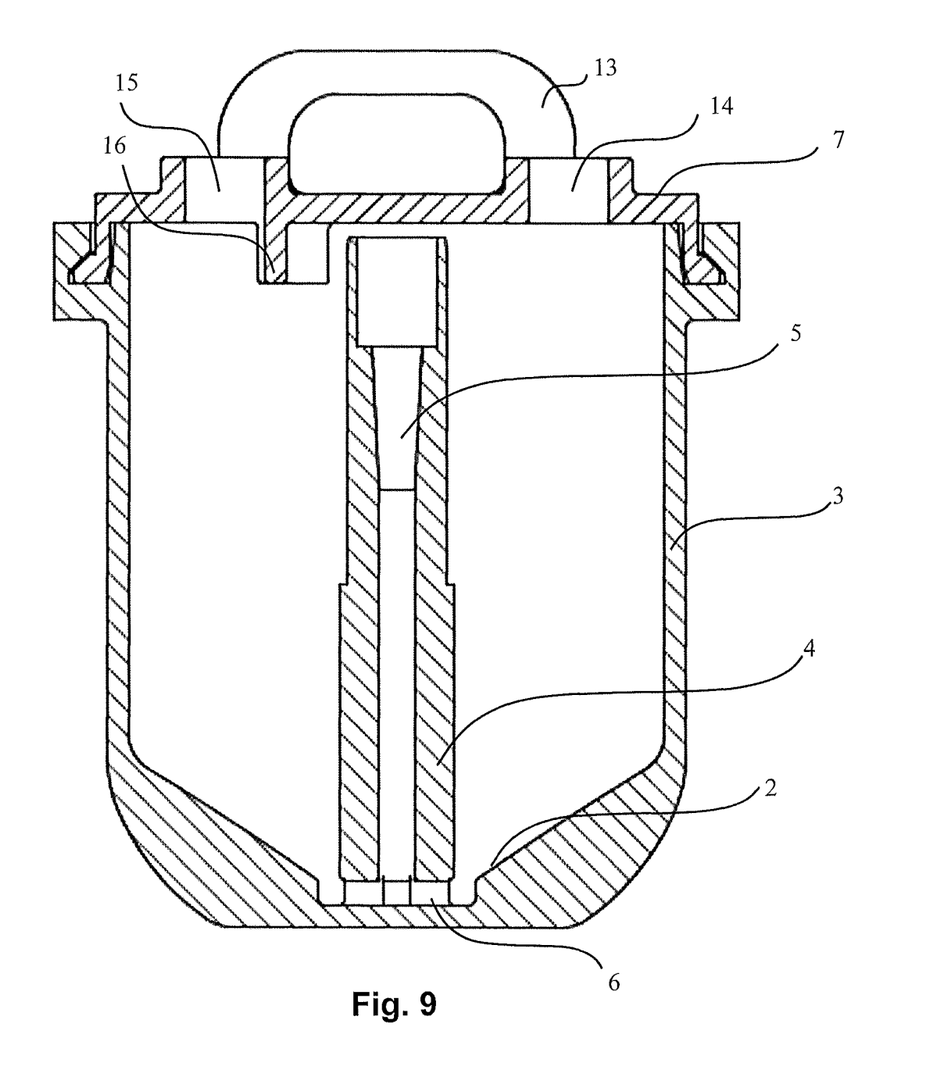
FIG. 9 is a cross-section view of the container according to the invention, which is closed with the lid.

As shown in FIGS. 8 and 9, a tube 4 passes through the centre of the container 1 coaxially aligned with it, the inner space of the tube 4 forming an outlet duct 5. Although in this exemplary embodiment, the tube 4 fits closely to the bottom 2 of the container 1 in its lowest area, the outlet duct 5 is in fluid communication with the space near the bottom 2 of the container 1 by means of openings 6 or grooves. Preferably, the container 1 has a recess (FIGS. 8 and 9) in its bottom 2 adjacent to the fluid communication of the container 1 with the outlet duct 5. Instead of the communication by means of the openings 6 or grooves, the fluid communication can be provided so that the tube 4 is attached in the container 1 in such a way that its lower end is arranged at a distance from the bottom 2 of the container, e.g. in case, when the tube 4 is attached to the side wall of the container 1. In such an embodiment the tube 4 with the outlet duct 5 is arranged eccentrically, or the outlet duct 5 is formed in the wall 3, alternatively in the reinforced wall 3 of the container 1. It is always preferred, if the bottom 2 at least partly slopes down towards the openings 6/grooves that connect the inner space of the container 1 with the inner space of the outlet duct 5. The outlet of the outlet duct 5 has a dead end and is adapted for the connection of a hose with the male-type connector or female-type connector for filling syringes, wherein the hose can be put on also by means of jumper, or the outlet part can be ended directly by an ending for connecting a syringe.

The upper end of the tube 4, or the upper end of the outlet duct 5, is arranged so that the material may be collected from the outlet duct 5.

Figure 7:
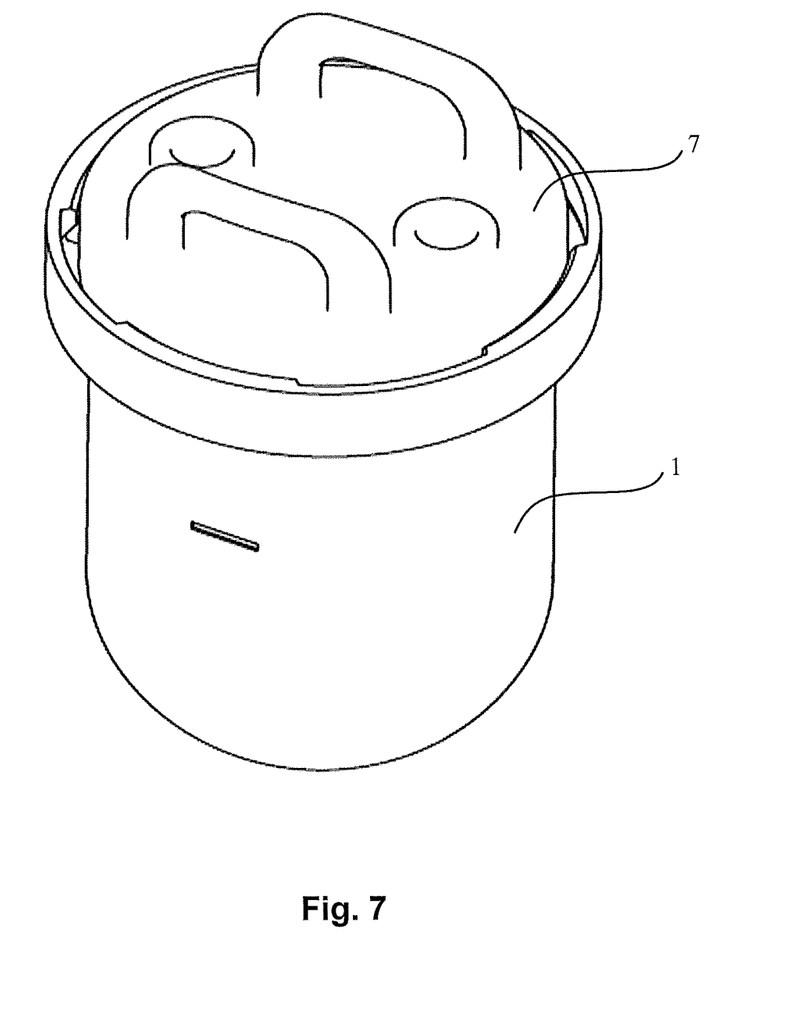
FIG. 7 shows the container according to the invention closed with the lid.

Preferably, the device also comprises the lid 7, with which it is possible to close the container 1 for transportation and especially for the processing of the material in the centrifuge. The lid 7 can be provided with a welded or removable sealing. In this exemplary embodiment the lid 7 as well as the container 1 are adapted for bayonet airtight attaching of the lid 7 to the container 1. The lid 7 is provided with two handles 13 on its upper side.

In a preferred embodiment, the lid 7 is provided with a barrier 16 on its lower side, the barrier 16 being arranged between the opening 14 for the biological material input and the output duct 5, namely for prevention of the outlet duct 5 contamination.

Further, the kit also comprises the separating float 8, the outer circumference of which corresponds to the inner circumference of the container 1 cross-section so that the separating float 8 may be insertable into the container 1 (at least up to a certain depth) in a similar way as a piston. In this exemplary embodiment, the tube 4 with the duct 5 is coaxially aligned with the container 1 and thus the separating float 8 has a pass-through opening 9 in its central part, through which the tube 4 passes while the separating float 8 is being inserted into the container 1. For determination of the maximum insertion of the float 8 into the container 1, preferably the outside diameter of the tube 4 is slightly enlarged in a given place, as can be seen in FIGS. 8 and 9.

In case the duct 5 is arranged in a different manner, the opening 9 in the separating float 8 is either arranged eccentrically or is completely omitted.

In the shown preferred embodiment, the walls of the pass-through opening 9, for the tube 4 to pass through, are elongated above the level of the separating float 8 and that way they facilitate guiding the separating float 8 in the container 1 in the direction perpendicular to the material surface.

Preferably, the separating float 8 is provided with at least one by-pass opening 10 for the material contained in the container 1 to be able to pass through the by-pass opening 10 while the separating float 8 is being inserted into the container 1 and in this way to get above the separating float 8. In a not-shown embodiment the by-pass openings 10 can be formed by notches and/or grooves near the outside circumference of the separating float 8 or in the area adjacent to the tube 4, alternatively they can be formed in such a way, that in at least one part of the separating float 8 they are not adjacent to the container 1 inside wall or to the outside wall of the tube 4.

At the same time, the separating float 8 has preferably at least one recess 11, wherein the by-pass openings 10 are arranged out of this recess 11, but preferably at its proximity. In the shown embodiment the by-pass openings 10 are arranged near the outside circumference of the separating float 8 that slopes down towards its centre or the outside walls of the pass-through opening 9, through which the tube 4 passes. However, a reversed or yet another arrangement is possible as well. For example, it is possible to form the separating float 8 so that, after having been inserted into the container 1, it forms an angle with the container 1 axis different from the right angle; that means that it passes askew and not perpendicularly to the container 1 axis. Such arrangement of the separating float 8 and its being guided in direction of the container 1 axis, i.e. in direction perpendicular to the surface of the material in the container 1, can be implemented, e.g., by means of appropriately adjusted guiding surfaces on the external circumference of the separating float 8 and/or (in the embodiment with the tube 4) on the pass-through opening 9 for the tube 4. In case of such an askew placing of the separating float 8, this separating float 8 implicitly slopes down towards the container 1 wall; the by-pass openings 10 can then be formed preferably on the opposite, i.e. the elevated side of the separating float 8.

In a preferred embodiment, shown in FIG. 8, the separating float 8 is provided with an auxiliary drainage channel 12 adjacently to the recess 11, the auxiliary drainage channel 12 being intended for collecting the material that has got above the separating float 8.

Preferably, the fluid communication of the lower end of the auxiliary drainage channel 12 with the space inside the container 1 above the separating float 8 is arranged in the area adjacent to the recess 11 or to the deepest part of the sloping area of the separating float 8. Preferably, the float 8 is made of a transparent or non-transparent plastic.

Preferably, materials of all parts of the device can be treated by autoclaving, i.e. they are thermostable. However, even materials for disposability of the device can be used.

In a preferred embodiment, the container 1 is made of transparent (clear, translucent) plastic. The lid can be made of transparent or non-transparent plastic. A metal is another material that can be used for the device, as well as the float.

The container 1 can be marked with a scale on its outer side for the biological material (e.g. lipoaspirate) volume determination, and a functional volume of the container 1 can be, e.g. within the range of 100 to 300 ml. As shown in FIG. 6, the container 1 is provided with a mark 17 indicating the minimum volume of the biological material in the container 1. The container 1 can be provided with a mark indicating the maximum volume of the biological material (not shown) in the container 1 as well.

The kit can further comprise a transparent plastic hose (not shown) with a connector for filling syringes, the hose being intended to be attached to the outlet of the outlet duct 5 of the collecting container 1 to suck out the so-called waste layers, i.e. the watery layer and the pellet layer. On one end the hose has a dead end or is provided with a male-type or female-type connector to be connected to the outlet duct 5 of the collecting container. On the other end the hose is ended by a luer lock connector with a foam lock preventing a return air intake (against the gravitation force), namely in case of a shorter variant of the hose. Or the hose is ended by a luer lock connector without the foam lock, in such a case the hose is longer so that, during collecting, it may be placed below the level of the material in the container 1. Alternatively even another type of the connector for filling syringes may be used.

Even though a particularly preferred exemplary embodiment and many possible adjustments and modifications thereof were described, it is evident that a person skilled in the art readily finds other possible alternatives of these embodiments. Accordingly, the scope of the patent protection is not limited to these exemplary embodiments, but rather it is defined by the attached claims.

The invention claimed is:

1. A kit for separation of the fluidal biological material, characterized in that it comprises
    a device for separation of a biological fluidal material, the device comprising:
        a container (1), which has a bottom (2) and a side wall (3), and
        an outlet duct (5) that is arranged in the container (1), the outlet duct (5) having an upper end adapted for collecting material from the outlet duct (5) and a lower end that is in fluid communication with the inner space of the container (1) at its bottom (2) and
    a separating float (8) for separating components of the fluidal biological material in the device for separation of a biological fluidal material, the separating float (8) comprising
        guiding surfaces to guide its movement when being inserted into the container (1) in the direction parallel to the axis of the inner space of the container (1), and
        at least one by-pass opening (10) for passage of the fluidal biological material contained in the container (1) from the space below the separating float (8) to the space above it.

2. The kit according to claim 1, characterized in that the bottom (2) of the device for separation of a biological fluidal material at least partly slopes down towards the area of fluid communication of the outlet duct (5) with the space at the bottom (2) of the container (1).

3. The kit according to claim 1, characterized in that the device for separation of a biological fluidal material comprises a tube (4), which is arranged in the container (1), wherein the internal cavity of the tube (4) forms the outlet duct (5).

4. The kit according to claim 3, characterized in that the tube (4) is coaxially aligned with the container (1).

5. The kit according to claim 3 characterized in that the tube (4), on its end facing the bottom (2) of the container (1), is provided with openings (6) and/or grooves for connection of the outlet duct (5) with the space at the bottom (2) of the container (1).

6. The kit according to claim 1, characterized in that the device for separation of a biological fluidal material further comprises a lid (7), which is detachably mountable to the container (1), the lid (7) being provided with an opening (14) for an entry of the biological material and an opening (15) for connection to a suction device that forms vacuum in the container (1).

7. The kit according to claim 1, characterized in that the separating float (8) comprises at least one recess (11) and/or at least partly slopes down to facilitate collection of the fluidal biological material from the space above the separating float (8).

8. The kit according to claim 1, characterized in that the separating float (8) comprises at least one auxiliary drainage channel (12) for collecting the material placed above the separating float (8), the lower end of the auxiliary drainage channel (12) being in fluid communication with the space above the upper surface of the separating float (8).

9. The kit according to claim 8, characterized in that the lower end of the auxiliary drainage channel (12) is in fluid communication with the space above the upper surface of the separating float (8) in the area of the recess (11) or in the area towards which the separating float (8) slopes down.

* * * * *